United States Patent
Williams et al.

(10) Patent No.: US 10,451,528 B2
(45) Date of Patent: Oct. 22, 2019

(54) COLLECTION, FILTRATION AND CONCENTRATION APPARATUS FOR BIOLOGICAL SAMPLES

(71) Applicant: ALPHA-TEC SYSTEMS, INC., Vancouver, WA (US)

(72) Inventors: Richard O. Williams, Vancouver, WA (US); Mark Williams, Vancouver, WA (US); John Kempke, Vancouver, WA (US)

(73) Assignee: Alpha-Tec Systems, Inc., Vancouver, WA (US)

( * ) Notice: Subject to any disclaimer, the term of this patent is extended or adjusted under 35 U.S.C. 154(b) by 558 days.

(21) Appl. No.: 14/993,979

(22) Filed: Jan. 12, 2016

(65) Prior Publication Data

US 2016/0341641 A1 Nov. 24, 2016

Related U.S. Application Data

(60) Provisional application No. 62/164,457, filed on May 20, 2015.

(51) Int. Cl.
| | |
|---|---|
| *G01N 1/00* | (2006.01) |
| *G01N 1/40* | (2006.01) |
| *B01L 3/00* | (2006.01) |
| *G01N 1/02* | (2006.01) |

(52) U.S. Cl.
CPC .......... *G01N 1/4077* (2013.01); *B01L 3/5021* (2013.01); *B01L 2200/025* (2013.01); *B01L 2200/0689* (2013.01); *B01L 2200/141* (2013.01); *B01L 2300/042* (2013.01); *B01L 2300/0681* (2013.01); *B01L 2300/0832* (2013.01); *B01L 2400/0457* (2013.01); *G01N 1/02* (2013.01); *G01N 2001/4088* (2013.01)

(58) Field of Classification Search
CPC .............. G01N 1/4077; G01N 1/02; G01N 2001/4088; B01L 3/5021; B01L 2200/025; B01L 2200/0689; B01L 2200/141; B01L 2300/042; B01L 2300/0681; B01L 2300/0832; B01L 2400/0457
USPC ........................................................ 422/549
See application file for complete search history.

(56) References Cited

U.S. PATENT DOCUMENTS

| | | | | |
|---|---|---|---|---|
| 4,081,356 | A * | 3/1978 | Zierdt | A61B 10/0038 209/17 |
| 4,675,110 | A * | 6/1987 | Fay | A61B 10/0038 210/436 |
| 4,902,421 | A * | 2/1990 | Pascale | B01D 29/01 210/416.1 |
| 5,508,175 | A | 4/1996 | Slifkin | |
| 5,556,544 | A | 9/1996 | Didier | |
| 6,296,763 | B1 | 10/2001 | Hicks | |
| 7,807,476 | B2 | 10/2010 | Pressman et al. | |
| 7,964,098 | B2 | 6/2011 | Williams | |

(Continued)

*Primary Examiner* — Jyoti Nagpaul
(74) *Attorney, Agent, or Firm* — McCoy Russell LLP

(57) ABSTRACT

The present disclosure describes a closed apparatus for collection, filtration and concentration of biological samples, such as fecal material. The sample is collected with an integrated sample collection device which introduces the sample into a transport liquid in a sample collection tube which couples to a filter unit coupled to a processing tube containing a processing liquid. The apparatus may be introduced into a centrifuge for centrifugal filtration.

20 Claims, 17 Drawing Sheets

(56) References Cited

U.S. PATENT DOCUMENTS 7,977,090 B2 7/2011 Hicks
2008/0251490 A1* 10/2008 Livingston .......... B01L 3/50825
215/253

* cited by examiner

COLLECTION, FILTRATION AND CONCENTRATION APPARATUS FOR BIOLOGICAL SAMPLES

FIELD OF INVENTION

The present description relates to a collection, filtration and concentration apparatus for biological samples.

BACKGROUND

Analysis of biological samples, such as fecal material, requires appropriate collection methods, optimum storage conditions, and careful handling during filtration and concentration to maintain the integrity of the microorganisms and analytes present in the sample, and to prevent the biohazardous components of the sample from contaminating the contact environment, including the equipment and the operator. Current practice involves collecting a sample, such as fecal material, in a specimen jar with a fixative liquid. The specimen jar with the sample is then transported to a laboratory where the sample is filtered and concentrated before it can be used for subsequent diagnostic and analytical procedures. The filtration of the sample involves removing the sample from the sample jar and transferring the sample to a filter unit with a filtrate collection tube. More than one filter unit may be used during the filtration process. Large debris and sediments may be removed first by passing the sample through a filter unit with large pore size followed by filtration through a filter unit with smaller pore size. The sample may be passed through the filter unit and into the collection tube via gravitational force and/or centrifugal force.

One example of a collection tube with a filter unit is illustrated in U.S. Pat. No. 6,296,763. A double receptacle filtration assembly has two open mouthed receptacles, a sample receptacle and a filtrate collection receptacle, configured to couple together through a hollow stopper containing a tubular filter. The sample is transferred from a specimen jar to the sample receptacle of the filter unit using a transfer device. The sample receptacle is then attached to the filter and the filtrate collection receptacle. The filter unit with the two receptacles attached is transferred to a centrifuge for filtration.

The inventors herein have recognized problems with the abovementioned filter unit, including additional handling of the biological sample required for transferring the sample from a separate sample specimen jar using a collection/transfer device into the filter unit, increasing the possibility of contamination of the contact equipment and operator. Also, additional reagents may be added to the sample and the sample filtrate for preserving and processing the sample, increasing the possibility of sample degradation and/or contamination of the contact environment.

To minimize sample handling during filtration and concentration of a biological sample, the inventors propose a sample collection, filtration and processing apparatus with a filter unit which may be coupled to a sample collection tube with an integrated sample collection device, and to a sample processing tube. One example of the apparatus may include a sample collection tube containing a transportation liquid with a first open end and a second open end opposite the first open end. The sample collection tube first open end may be configured to couple to a first removable cap. The first removable cap may have an integrated sample collection device. The apparatus may include a sample processing tube containing a processing liquid with a sample processing tube first open end and a sample processing tube second closed end opposite the processing tube first open end. The apparatus may include a matched filter unit with a first open end and a second open end opposite the filter unit first open end. The filter unit first open end may be configured to couple to the collection tube first open end, and the filter unit second open end may be configured to couple to the processing tube open end.

In one example of using the above described sample collection, filtration, and concentration apparatus, the sample may be collected with a collection device coupled to a first removable cap. The first removable cap may couple to a sample collection tube first open end, where the coupling may introduce the sample and the sample collection device into a transport liquid in the sample collection tube. A matched filter unit may be coupled to an open end of a processing tube containing a processing liquid to form a filtration-processing unit, followed by removal of the first removable cap from the sample collection tube first open end. The filtration-processing unit may subsequently be coupled to the sample collection tube first open end such that the filtration-processing assembly may align with and close the collection tube first open end. The sample may now be filtered from the sample collection tube, through the filter unit and in to the processing tube.

Thus, the sample collection, filtration, and processing apparatus described above enables direct collection and transfer of a sample to the sample collection tube using the integrated sample collection device of the apparatus, eliminating the need for a separate sample specimen jar and additional transfer device. The sample collection tube of the apparatus containing a pre-measured volume of a transport liquid and the processing tube containing a pre-measured volume of processing liquid, eliminates the need to introduce additional reagents into the apparatus, further reducing sample handling and contamination.

DETAILED DESCRIPTION

The present application relates to an apparatus for collecting, filtering, and concentrating biological samples. The apparatus may include a sample collection tube containing a transport liquid, coupled to a removable cap with an integrated sample collection device. The sample collection tube may also couple to a filter unit which may couple to a sample processing tube containing a processing liquid.

Figure 1:
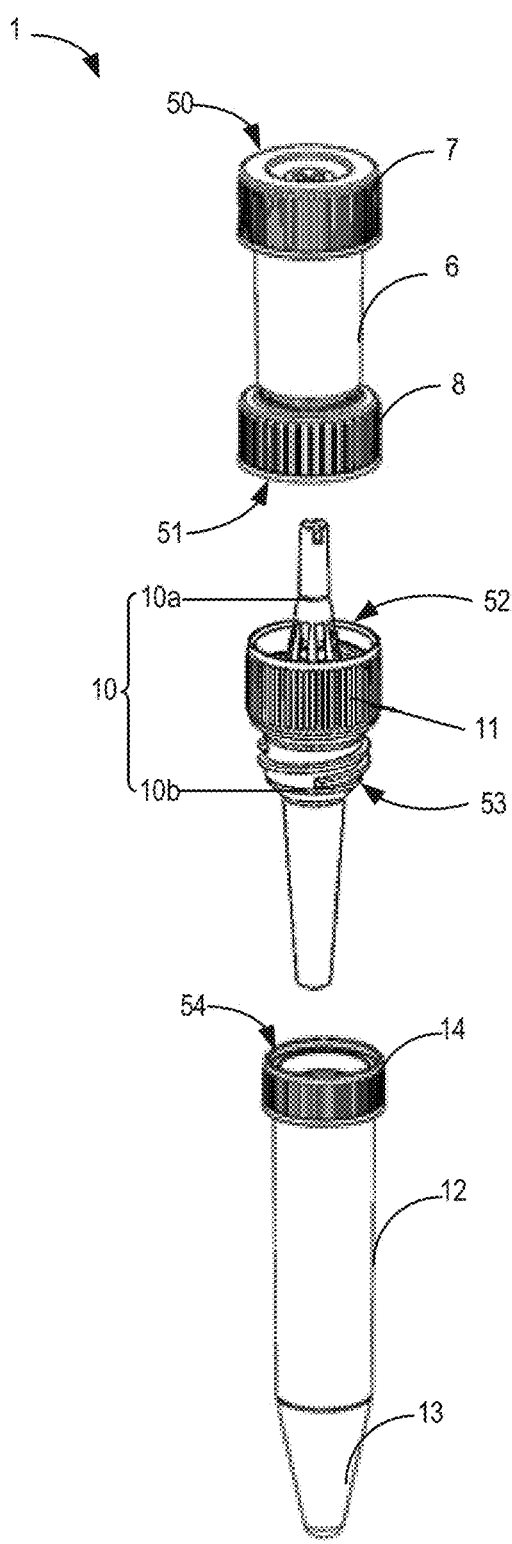
FIG. 1 shows a perspective view of a collection, filtration and concentration apparatus for biological samples.
Figure 2:
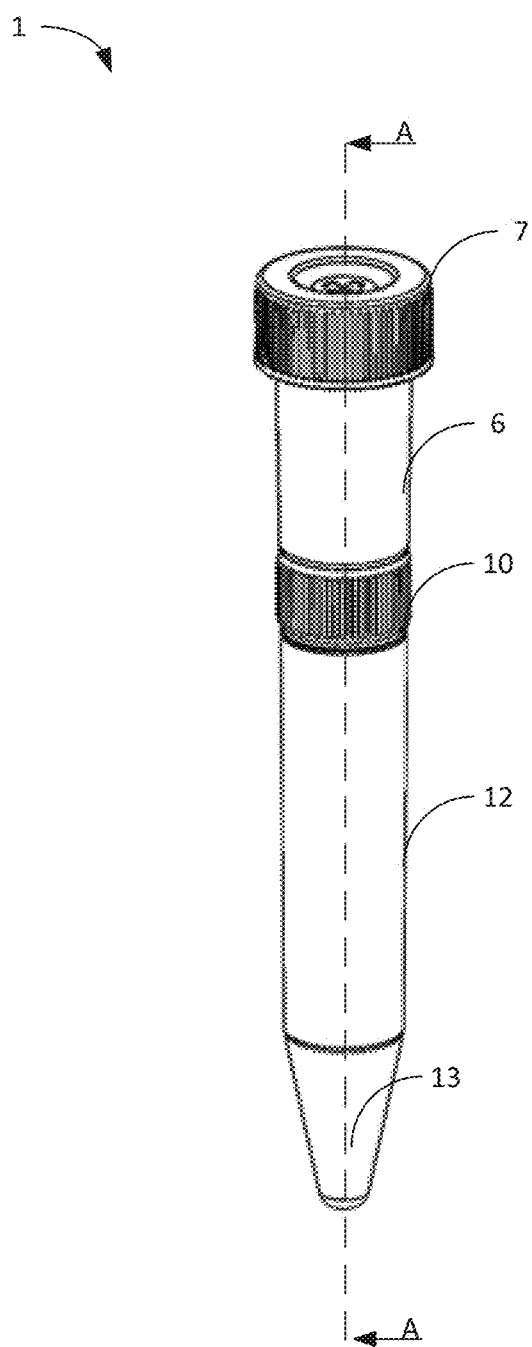
FIG. 2 is a perspective view of the sample collection, filtration and concentration apparatus of FIG. 1 with the sample collection tube and the processing tube coupled to the filter unit.
Figure 3:
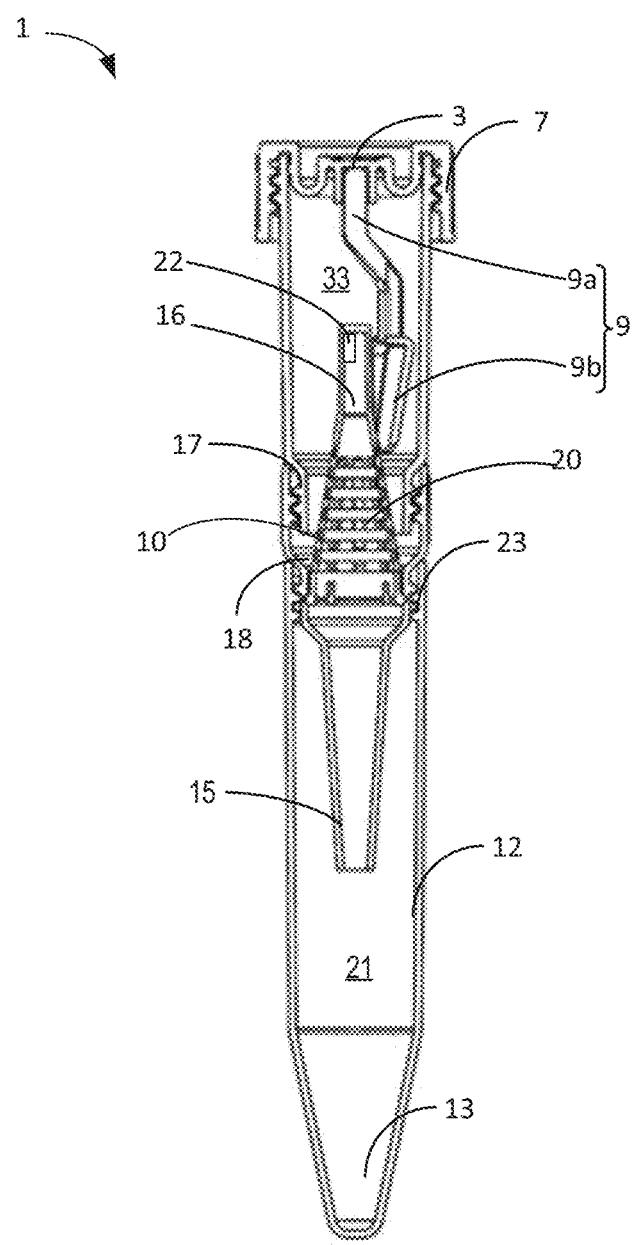
FIG. 3 is a cross-sectional view of the apparatus of FIG. 2 along the lines marked A-A.
Figure 4:
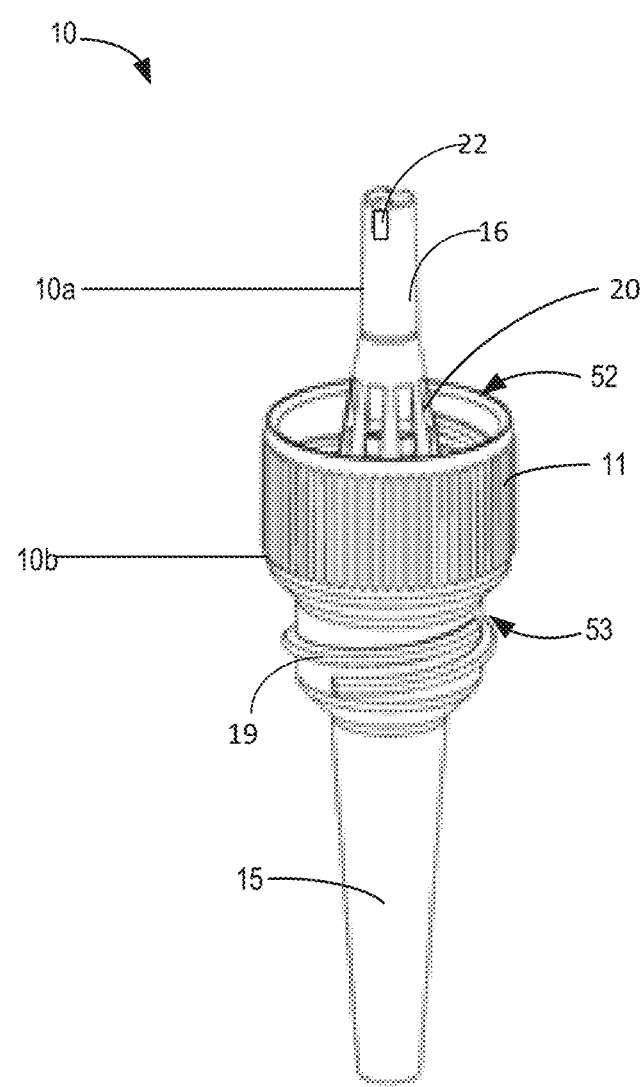
FIG. 4 shows a perspective view of a filter unit of the apparatus of FIG. 1.
Figure 5:
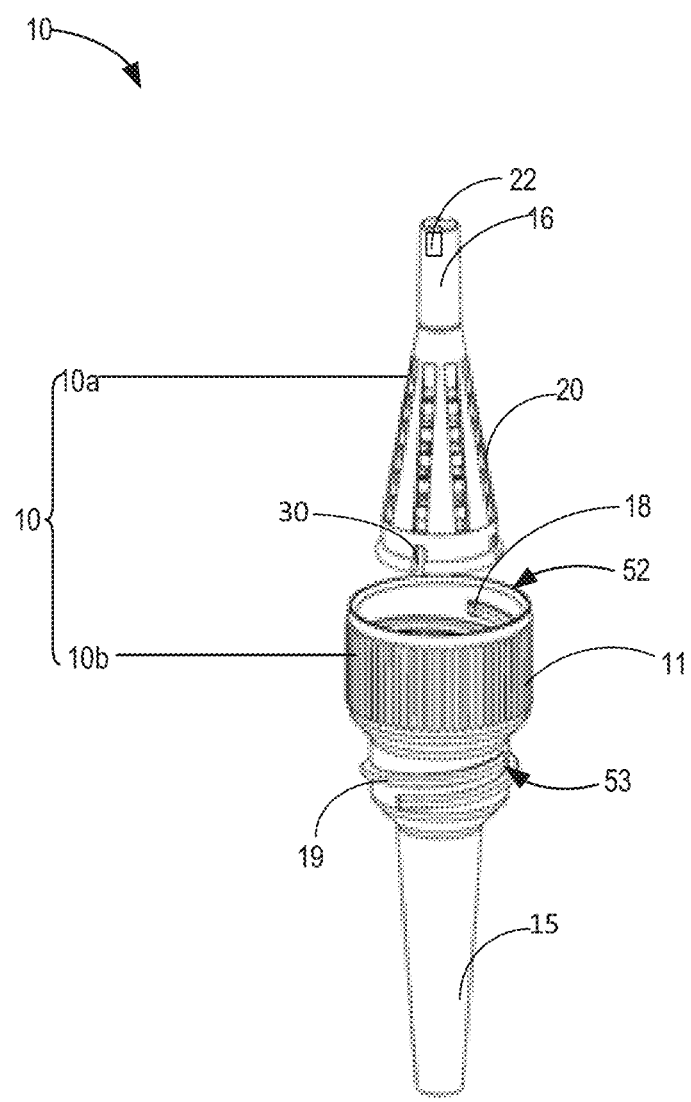
FIG. 5 is an exploded view of the filter unit of FIG. 4 with a conical filter top and a filter base.
Figure 6:
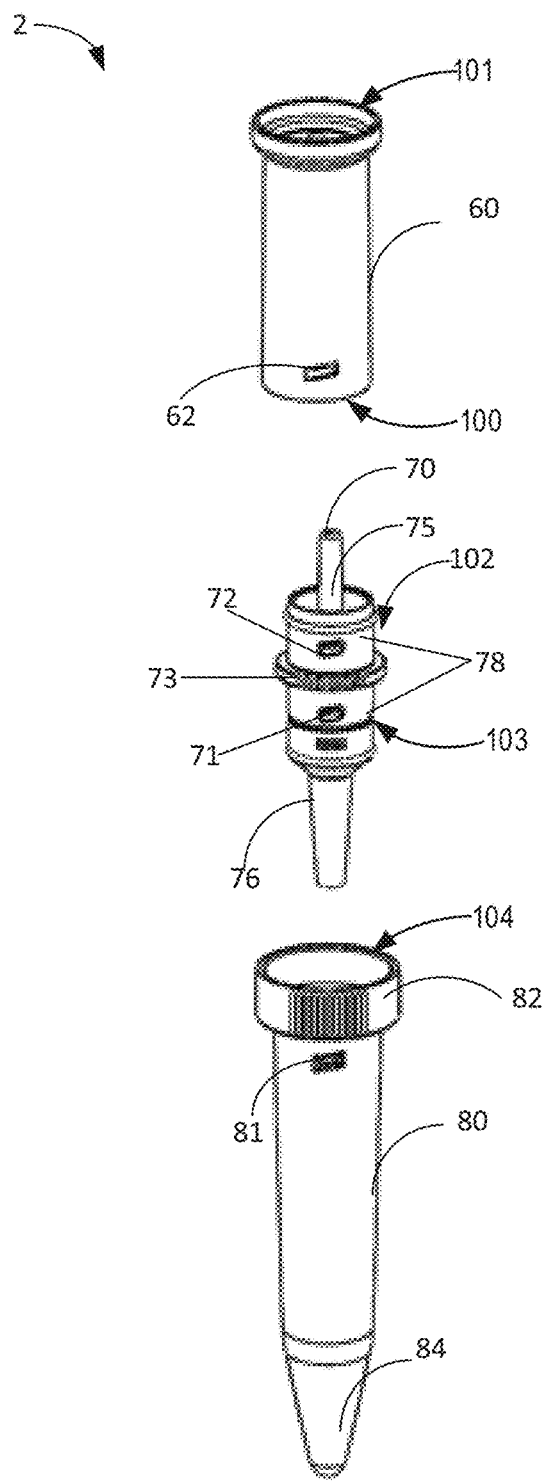
FIG. 6 shows another embodiment of a sample collection, filtration and concentration apparatus.
Figure 7:
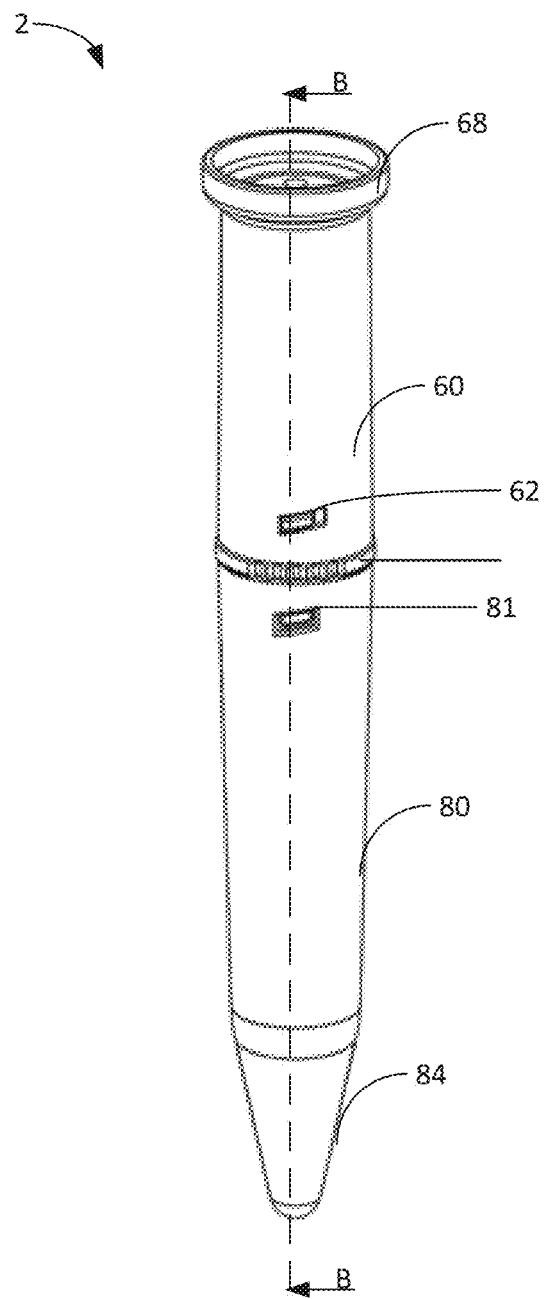
FIG. 7 shows a perspective view of the apparatus of FIG. 6.
Figure 8:
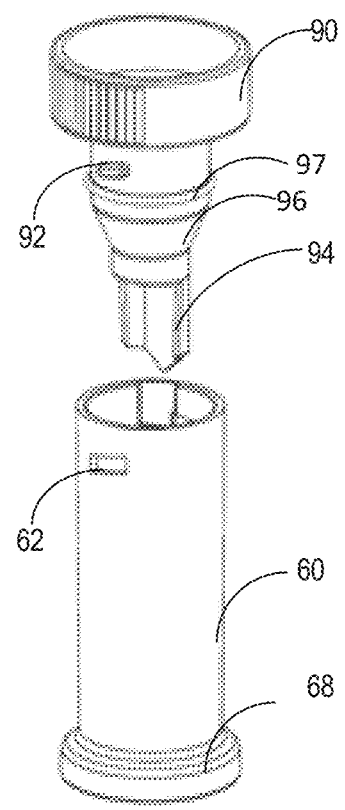
FIG. 8 is a perspective view of the sample collection tube of FIG. 6 with a removable cap coupled to a sample collection device.
Figure 9:
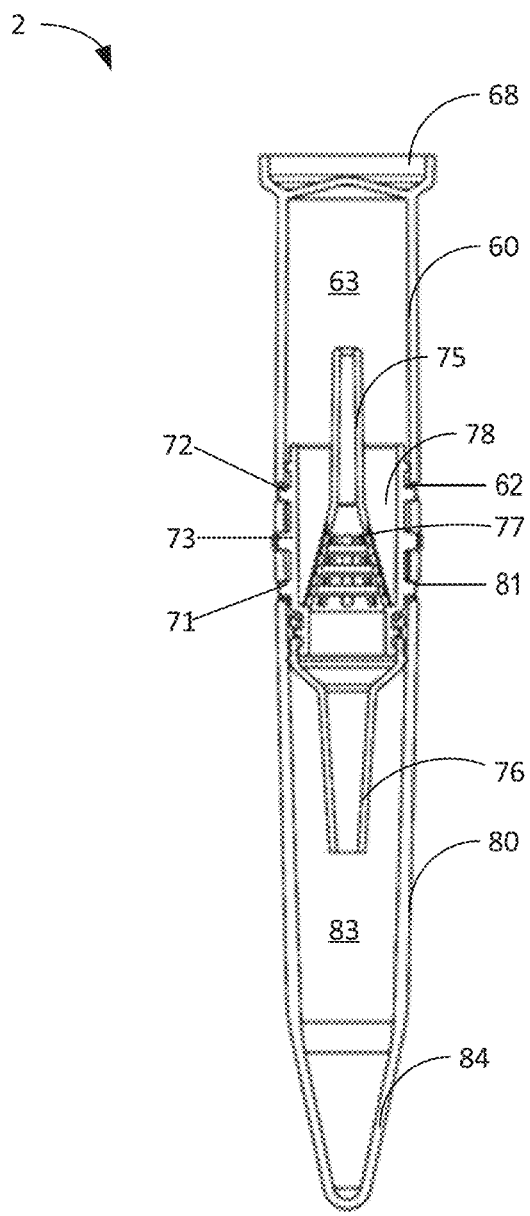
FIG. 9 is a cross-sectional view of the apparatus of FIG. 7 along the line marked B-B.
Figure 10:
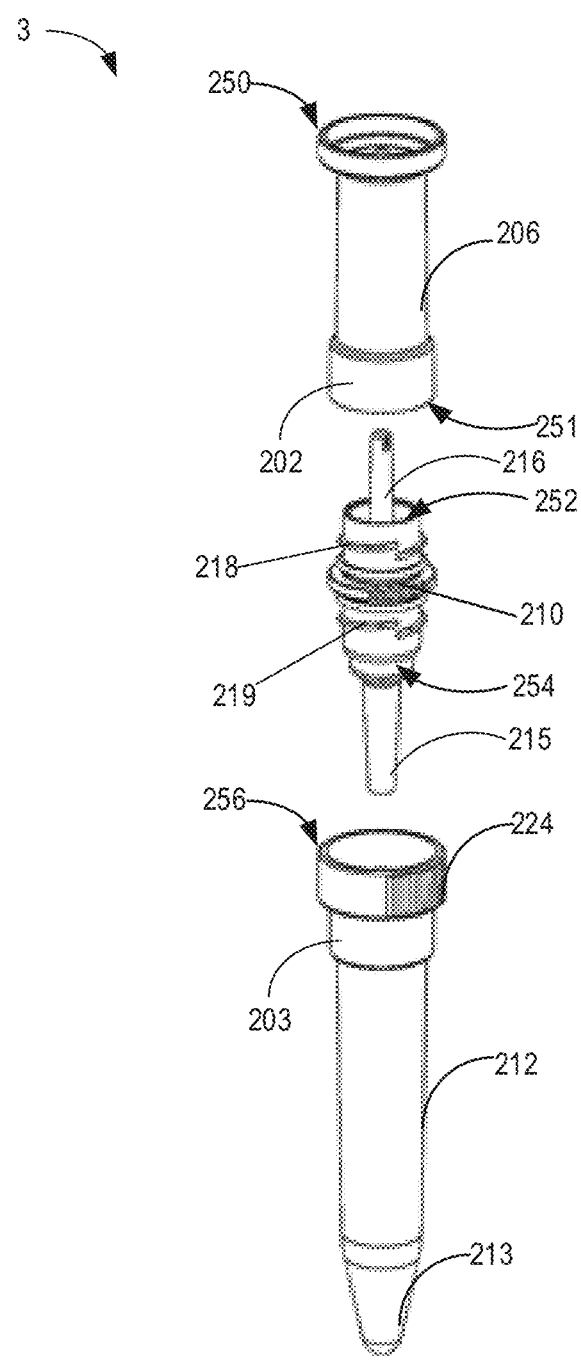
FIG. 10 shows an embodiment of a sample collection, filtration, and concentration apparatus.
Figure 11:
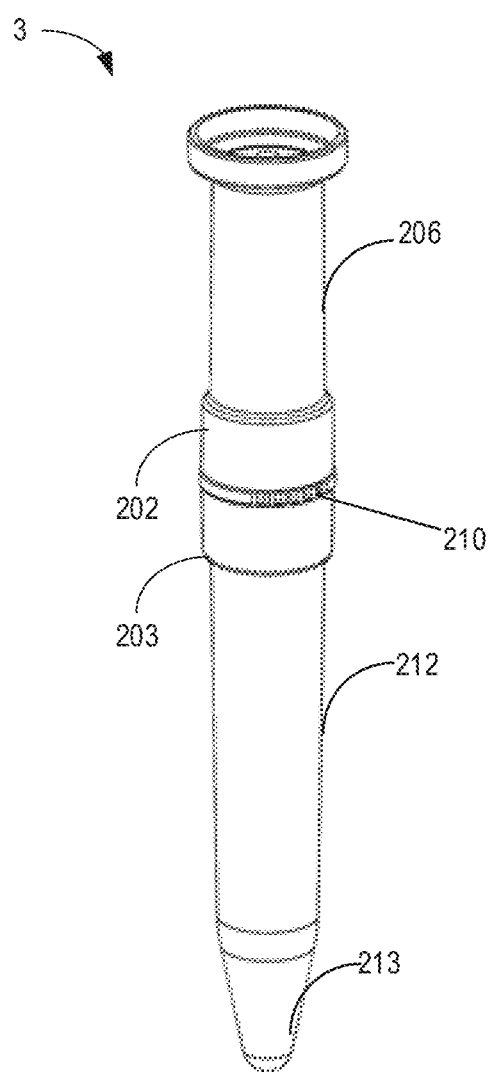
FIG. 11 is a perspective view of the assembled apparatus of FIG. 10.
Figure 12:
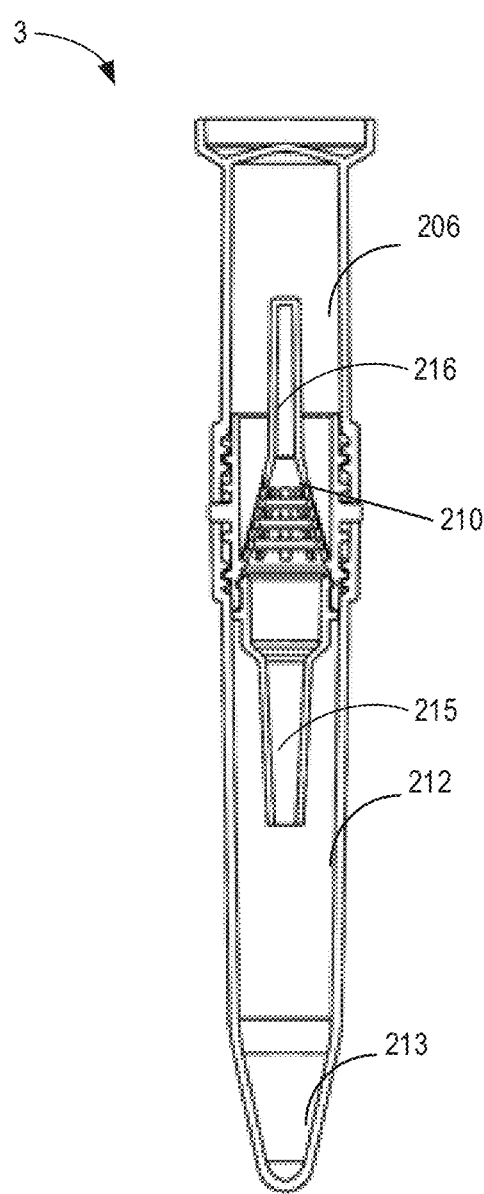
FIG. 12 is a cross-sectional view of the assembled apparatus of FIG. 11.
Figure 17:
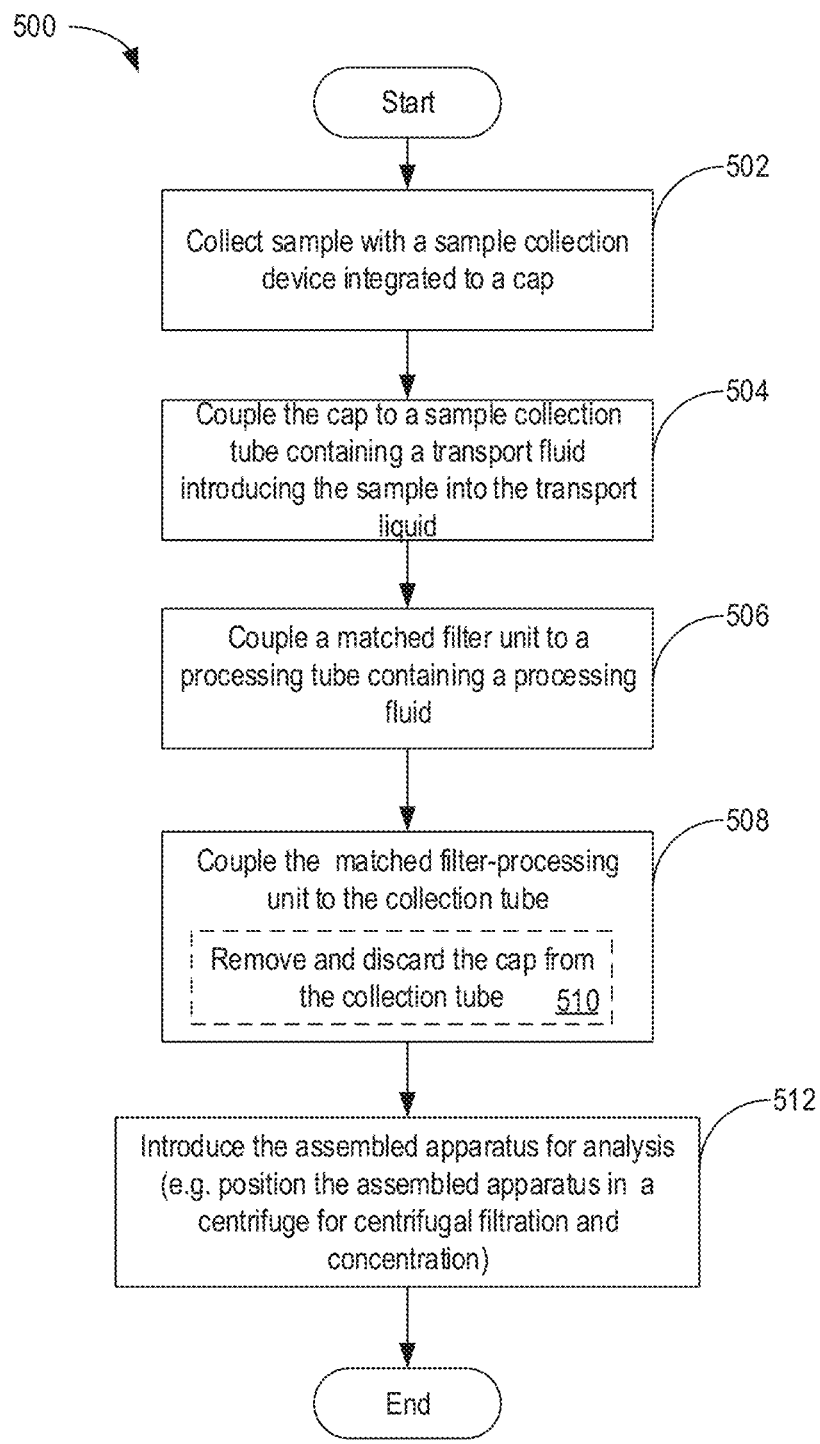
FIG. 17 is a flowchart of a method for collecting, filtering and concentrating a biological sample.

In one non limiting example, the filter unit may include a substantially conical shaped filter top integrally attached to a filter base. In some embodiments, the filter top with the conical shape filter may also have a gas exchange stem and gas vents. The sample may be filtered from the sample collection tube, through the sample filter unit and received into the sample processing tube, where the sample may be processed further or stored for subsequent analysis. The filter unit coupled to the sample collection tube and the processing tube may be a closed unit which may be introduced into a centrifuge for centrifugal filtration. FIGS. 1-2 illustrate example apparatus 1 for collecting, filtering, and concentrating biological samples. FIG. 3 shows a cross sectional view of the assembled apparatus of FIG. 2 along a line marked A-A. Apparatus 1 may be used for collection and transport of biological samples in a transportation liquid, for filtering the collected sample through a filter unit, and for concentrating the sample filtrate collected in a sample processing tube containing a processing liquid. FIGS. 4 and 5 illustrate an example filter unit of the apparatus of FIG. 1. FIGS. 6 and 7 show another embodiment of an apparatus for collecting, filtering, and concentrating biological samples. FIG. 8 shows a sample collection tube of the apparatus of FIG. 6. FIG. 9 shows a cross-sectional view of the apparatus of FIG. 7 along line marked B-B. FIGS. 10-12 illustrate another embodiment of the sample collection, filtration and concentration device. FIGS. 13-16 show an embodiment of the sample collection, filtration, and concentration apparatus with a frangible seal in the sample collection tube and a puncturing element in the filter unit to puncture the frangible seal. The embodiments illustrated in FIGS. 1-16 are drawn approximately to scale, although various modifications in the relative sizing of one or more components may be made. FIG. 17 shows a method for collecting, filtering and concentrating a biological sample. For purpose of discussion, FIGS. 1-5 will be described collectively. As described above, the sample collection, filtration and concentration apparatus 1 may include a sample collection tube 6 with an integrated sample collection device 9 and a sample processing tube 12. The sample collection tube 6 and the sample processing tube 12 may be configured to couple to a matched filter unit 10, as illustrated in FIGS. 1-3.

The sample collection tube 6 of apparatus 1 may have a first open end 50 configured to couple with a first removable cap 7. In one example illustrated in FIG. 3, the first removable cap 7 may have an integrated sample collection device 9. The sample collection device 9 may function to collect a sample and transfer it to the sample collection tube 6. In one example, the sample collection device 9 integrated to the removable cap 7 may be received in the sample collection tube 6 upon coupling of the first removable cap 7 to the sample collection tube first open end 50, as shown in FIG. 3. In another example, the sample collection device 9 may be releasable from the removable cap 7 into the sample collection tube 6 without coupling the removable cap 7 to the sample collection tube. In a further example, the sample collection device 9 may be released from the removable cap 7 after coupling of the removable cap 7 to the collection tube 6. In other examples, only part of the sample collection device 9 may be releasable from the removable cap 7 before or after coupling of the removable cap 7 to the sample collection tube 6.

The sample collection device 9 of apparatus 1 may be a shank 9a terminating in a scoop 9b, as illustrated in FIG. 3. The sample collection device 9 with the shank 9a ending in a scoop 9b may function as a mechanism for sample collection and transfer. In other examples, the sample collection device 9 may be shank terminating in a spoon, a fork, a spatula, or a collection retaining form to enable sample collection and sample transfer. In one embodiment, the sample collection device 9 may be only a collection retaining form, such as a scoop, a spoon, a fork, without a shank.

Upon coupling of the sample collection tube 6 and the first removable cap 7, the integrated sample collection device 9 with the shank 9a ending in a scoop 9b may be introduced into a work space 33 in the sample collection tube 6. FIG. 3 illustrates an example of the collection device 9 introduced into the work space 33 of the sample collection tube 6. The work space 33 of the sample collection tube 6 may contain a transport liquid. In one embodiment, the scoop 9b of the sample collection device 9 introduced into the sample collection tube 6 may reach mid-way into the sample collection tube workspace 33. In another example, the scoop 9b of the sample collection device 9 may reach all the way to the bottom of the sample collection tube work space 33.

FIG. 3 illustrates an example of the collection device 9 with one end of the shank 9a integrated to the removable cap 7. A socket 3 on the removable cap 7 may secure the sample collection device 9 to the removable cap 7. The socket 3 on the removable cap 7 may form a contact sharing complementary interlock with the shank 9a inserted into the socket 3. In one example, the socket 3 and the inserted shank 9b may be glued together to produce greater adhesion. In another embodiment, the socket 3 and the inserted shank 9b may have mating threads on the contact sharing surfaces for reversible coupling. In further examples, a twist-lock mechanism of coupling between the socket 3 and the inserted shank 9b may be used to secure the shank 9b to the removable cap 7. The position of the socket 3 on the removable cap may vary. In one example the socket 3 may be in the center of the removable cap 7, while in other embodiments the socket 3 on the removable cap 7 may be off-center.

The apparatus 1 may be used for filtering biological samples, such as fecal material. In another example, the biological sample may be a tissue. In yet another example, the sample may be mucous discharge. The biological sample may be of human origin. In another example, the biological sample may be of animal origin. The sample collection tube 6 of apparatus 1 may contain a premeasured amount of a transport liquid to store and transport the biological sample. The choice and volume of transport liquid may depend on the sample analysis parameters and requirements. In one example, the transport fluid may prevent degradation of the biological sample. In a further example, the transport liquid may be a fixative used for fecal samples to preserve cysts, eggs and larvae of most parasites found in fecal sample for subsequent examination and concentration. In one example, the fixative may be formalin or a solution containing formalin such as sodium acetate/acetic acid/formalin, or merthiolate/iodine/formalin. In other examples, the fixative may be mercuric chloride, PVA, or a single vial universal fixative. In another example, the transport liquid may be a diluent, such as saline. In yet another example, the transport liquid may be a cryoprotectant to preserve the biological sample constituents, such as microorganisms, if the sample is frozen. In a further example, the transport liquid may be a mix of two or more liquids, such as one part formalin mixed with one part saline.

The sample collection tube 6 may also have a second open end 51, opposite to the sample collection tube first open end 50, which may be configured to couple to a second removable cap 8, as illustrated in FIG. 1. In one embodiment, the second removable cap 8 may have flared fitting, wherein the second removable cap 8 may have a slightly larger circumference than the sample collection tube 6, beyond the coupling interface of the sample collection tube second open end 51 and the second removable cap 8. In one example, the removable cap 8 with a flared fitting may be attached to the sample collection tube second open end 51. The flared removable cap 8 may be a base for standing the sample collection tube 6 upright on a level surface. The removable cap 8 acts as a flared base for standing the sample collection tube 6 may be particularly useful while opening and closing the sample collection tube first open end 51 to receive the sample collection device and for attaching a filter unit to the sample collection tube.

FIGS. 1-3 illustrate and example of the processing tube 12 of apparatus 1. The processing tube 12 receives the sample filtrate passed from the sample collection tube 6 through the filter unit 10. The processing tube 12 may have a conical shaped closed bottom 13 and a processing tube open end 54 opposite the closed bottom 13, configured to reversibly couple with a third removable cap 14. In one embodiment, a pre-measured volume of processing liquid may be present in the processing tube 12. In one example, the processing liquid may enable concentration of the sample filtrate by separating the filtrate components based on the respective density of each filtrate component. One example of a processing liquid may be formalin-ethyl acetate for sedimentation concentration of parasites in a biological sample. In another example, a nucleic acid precipitation and extraction buffer may be the processing liquid to extract nucleic acids from the sample constituents.

The outer surface of the processing tube open end 54 may be configured to couple with the third removable cap 14 to close the processing tube 12 to form a liquid tight seal, as illustrated in FIG. 1. In one example, the third removable cap 14 may be coupled to the processing tube 12 before filtration to prevent spilling and/or contamination of the processing liquid inside the processing tube 12. In another example, after the sample filtrate is received in the processing tube 12, the third removable cap 14 may be coupled to the processing tube 12 to store the sample filtrate for subsequent analysis. The inner surface of the processing tube open end 54 may be configured to couple with the filter unit 10 to form a liquid tight seal.

FIGS. 4 and 5 illustrate and example of the filter unit 10 of the sample collection, filtration and concentration apparatus 1. The filter unit may have a filter top 10a and a filter base 10b, integrated together to form the filter unit 10. In one example, the filter top 10a and the filter base 10b may be integrated by a twist-lock mechanism, wherein openings 30 (shown in FIG. 5) on the filter top 10a may mate with locking lugs (not shown) in the filter base, securing the filter top to the filter base. Other mechanisms of coupling, such as corresponding male and female threads in the filter top 10a and the filter base 10b may couple the filter top 10a to the filter base 10b. In other embodiments, the filter top 10a and the filter base 10b may be glued together to form the filter unit 10.

The filter unit 10 may have a frictional gripping surface 11 on its outer circumference, as illustrated in an example in FIGS. 1-5. The gripping surface 11 may be used to promote grasping of the filter unit 10 and of the apparatus 1 during coupling and un-coupling of the filter unit 10 to the sample collection tube 6 and to the processing tube 12. In order to enhance hand grip and to maximize ease of twisting motion, the frictional gripping surface 11 may be comprised of a plurality of linear parallel ridges.

The filter top 10a may include a conically-shaped filter 20 and a hollow gas exchange stem 16. The surface of the filter 20 may be conical in shape with steeply inclined walls which may provide a greater filter surface area than a circular disc shaped filter. In one non-limiting example, the slope of the filter 20 may be between 10 and 15 degrees. In other examples, the slope may be higher than 15 degrees. In other examples, the slope may be less than 10 degrees. In one non-limiting example, the slope of the filter 20 may be between 10 and 15 degrees. In other examples, the slope may be higher than 15 degrees. In other examples, the slope may be less than 10 degrees.

In one embodiment, the pores in the filter 20 of the filter unit 10 may allow microorganisms in a biological sample to pass through the filter 20, and may exclude any particulate debris in the sample from filtering. The size of the pores in the filter 20 may determine the kind of microorganisms which will pass through the filter. In one example, a filter pore size of 2 micron will allow most parasites, bacteria, and viruses to pass through the filter 20. In another example, a filter pore size of 0.45 micron will exclude most parasites and many bacteria from passing through the filter, while all viruses will pass through the pores.

The distal end of conical filter 20 may be joined to a gas exchange stem 16. The gas exchange stem 16 may be formed by a hollow tube which may be vented at its apex with a plurality of radially arranged gas exchange vents. A representative gas exchange vent 22 is shown in FIGS. 3-6. It is to be understood that more than one gas exchange vent may be present, such as four vents equally distributed on the gas exchange stem 16. The gas exchange stem 16 and the gas vent 22 help equalize gas pressure during this filtration and prevent blockage of the filter 20. In one embodiment, the gas exchange stem 22 may be conical. In one example, the gas exchange vent 22 may be oriented at the steep angle of the conical shape of the gas exchange stem 16 to allow for potentially clogging debris to slide away from the gas exchange vent 22.

The matched filter unit 10 may have mechanisms and dimensions which may allow coupling of the filter unit 10 to the sample collection tube 6 and to the sample processing tube 12. Coupling of the filter unit 10 matched to the sample collection tube 6 and to the sample processing tube 12 may be enabled by various mechanisms of reversible mating. In one embodiment, a filter unit first open end 52 may be configured to couple with the sample collection tube first open end 50. In another embodiment, the filter unit first open end 52 may couple with the sample collection tube second open end 51. In one example, the internal portion of the filter base 10b of the filter unit 10 may be comprised of female threads 18 which may fittingly engage the male threads 17 on the outer surface of the sample collection tube first open end 50, coupling the filter unit 10 to the sample collection tube 6, as shown in FIG. 3. In another embodiment, the first set of female threads 18 on the filter unit 10 may fittingly engage the male threads on the outer surface of the collection tube second open end 51, coupling the filter unit 10 to the sample collection tube second open end 51.

In one embodiment illustrated in FIG. 3, coupling of the sample collection tube 6 with the filter unit 10 introduces the filter 20 and the gas exchange stem 16 with gas vent 22 inside the sample collection tube 6 work space 33. The gas exchange stem 16 with a hollow tube and the gas vent 22 may help equalize gas pressure during filtration and prevent blockage of the filter 20. In one example, the gas exchange stem may extend to the middle of the work space 33. In other embodiments, the gas exchange stem 16 may extend beyond the midpoint of work space 33.

A filter unit second open end 53 opposite to the filter unit first open end 52, may be configured to couple to the sample processing tube 12, securing the filter unit 10 to the processing tube 12. In one embodiment, the filter unit 10 may have male mating threads 19 on the filter base 10b configured to couple with female threads 23 in the inner wall of the processing tube 12, as illustrated in FIG. 3. It may be noted that mating threads or any other reversible complementary mating mechanisms forming a liquid tight seal, such as interlocking groove and protrusions, may be used to couple the filter unit 10 to the sample collection tube 6 and the sample processing tube 12.

Referring to FIGS. 1, 3, 4 and 5, the filter base 10b may have an elongated funnel stem 15. Upon coupling of the filter unit 10 to the processing tube 12, the funnel stem 15 may be introduced and received inside the processing tube work space 21, as shown in FIG. 3. The funnel stem 15 may collect the sample filtrate dispensed through the filter 20 and discharges the filtrate towards the conical bottom 13 of the processing tube 12. In some examples, the funnel stem 15 may include spill prevention structures such that the funnel stem may be configured such that upon inversion of the apparatus 1, liquid within the processing tube work space 21 may be prevented from spilling out.

Thus, the above described apparatus 1 for collection, filtration and concentration of biological samples, may include the filter unit 10 coupled to the sample collection tube 6 containing a transport liquid and coupled to the processing tube 12 containing processing liquid. The apparatus 1 eliminates the requirement for additional sample collection jar, separate sample collection/transfer device, and additional liquids for transportation and processing of a biological sample. The apparatus 1 also reduces sample handling, thereby decreasing the possibility of contamination of the sample and the contact environment.

FIGS. 6-9 illustrate another embodiment of a sample collection, filtration, and concentration apparatus, substantially similar to the above described apparatus 1 but with a twist-lock mechanism of coupling a filter unit to a matched sample collection tube and to a matched processing tube. In such examples, the locking tabs may engage in slots on the tube and allow the cap to be inserted and tightened similar to a threaded cap. It should be appreciated that the example is provided for illustration purposes. Other lock mechanisms are also considered, including, but not limited to, twisted caps, snap-locks, etc. For purpose of discussion, FIGS. 6-9 will be described collectively.

An embodiment of a sample collection, filtration, and concentration apparatus 2 may include a filter unit 70 with two open ends. A filter unit first open end 102 may couple by twist-lock mechanism to a sample collection tube 60 containing a transportation liquid. A filter unit second open end 103 opposite filter unit first open end 102 may couple by twist-lock mechanism to a sample processing tube 80 containing a processing liquid.

The sample collection tube 60 of apparatus 2 may have an open end 100 and a closed end 101 opposite to the sample collection tube open end 100, as illustrated in FIGS. 6-9. The sample collection tube open end 100 may be configured to couple with a first removable cap 90 with an integrated sample collection device 94, as shown in FIG. 8. In one embodiment, the first removable cap 90 with an integrated sample collection device 94 may couple with the sample collection tube 60 by twist-lock mechanism. In one example, a locking lug 92 extends radially outwards from on the base of first removable cap 90. Upon coupling of the first removable cap 90 with the integrated sample collection device 94 to the sample collection tube 60 to transfer the collected sample into a transport liquid, the locking lug 92 may be received by a complementary opening 62 on the collection tube first open end 100, forming a liquid tight seal. In one embodiment, a plurality of radial locking lugs may be present on the base of the first removable cap 90 that may twist-lock with a plurality of complementary openings on the sample collection tube upon coupling of the removable cap 90 to the sample collection tube 6.

The removable cap 90 may be integrated to a sample collection device 94, as illustrated in FIG. 8. In one embodiment, the sample collection device 94 may be integrated to the removable cap 90 through a conical connecting piece 96 with a plurality of concentric ridges 97. In one example, the conical connecting piece 96 with the concentric ridges 97 may plug the sample collection tube open end 100 when coupled to the sample collection tube 60. A liquid tight seal may be formed between the contact surfaces of the sample collection device 94 and the inner wall of the sample collection tube open end 100. In a further example, the integration of the sample collection device to the removable cap 90 may be through a cylindrical connecting piece. The sample collection device 94 may be a collection retaining form, such as a scoop, a spoon, or a fork. In one embodiment the sample retaining form may be directly integrated to the removable cap. In a further example, the collection retaining form may be integrated to the removable cap via a shank.

The sample collection tube closed end 101 may have a wide base 68, such that the circumference of the wide base 68 may be slightly more than the circumference of the sample collection tube 60. In one example, the wide base 68 may be used to stand the sample collection tube 60 in an upright orientation. The sample may be stored and transported in the sample collection tube 60 containing the transport liquid with the first removable cap 90 coupled to close the collection tube open end 100. The sample may be subsequently filtered through a filter unit 70.

The filter unit 70 of apparatus 2 may have a conical shaped filter 77 with a gas exchange stem 75 to equalize pressure between two attached tubes during filtration, and a conically shaped funnel stem 76 to receive the sample filtrate passed through the filter 77, as shown in FIGS. 7 and 9.

The filter unit 70 may have a frictional gripping surface 73 encircling the filter unit outer wall, as illustrated in FIGS. 6 and 7. The frictional gripping surface 73 of apparatus 2 may be similar to the frictional gripping surface 11 of apparatus 1, shown in FIGS. 1 and 2. The frictional gripping surface 73 may be particularly useful for gripping the filter unit 70 and the apparatus 2 during coupling and uncoupling procedures.

In one embodiment illustrated in FIGS. 6 and 9, the filter unit 70 may be partly encased in a cylindrical chamber 78. The circumference of the encasing cylindrical chamber 78 around the filter unit 70 may be slightly less than the circumference of the sample collection tube open end 100 and the processing tube open end 104. In one example illustrated in FIG. 9, coupling of the filter unit 70 with the sample collection tube open end 100 introduces part of the cylindrical chamber 78 into the sample collection tube open end 100 and the interfacing surfaces may form a tight fit, preventing the sample and the transport liquid from leaking out of the sample collection tube 60. Similarly, coupling of the filter unit 70 to the processing tube 80 may introduce the encasing chamber 78 into the processing tube open end 104, forming a tight fit and preventing the processing liquid from leaking out of the processing tube 80.

Referring to FIGS. 6 and 9, the encasing chamber 78 may have a protruding locking lug 72 at the filter unit first open end 102 and a protruding locking lug 71 on the filter unit second open end 103 opposite the filter unit first open end 102. In one embodiment, the locking lug 72 may couple the filter unit first open end 102 to the collection tube open end 100 by a twist-lock mechanism. The filter unit first open end 102 locking lug 72 may be received by complementary opening 62 on collection tube open end 100 when the removable cap with integrated device is removed, as shown in FIG. 9. Similarly, the locking lug 71 may couple the filter unit second open end 103 to the processing tube 80 by twist-lock mechanism. In one example, the locking lug 71 on filter unit 70 may be introduced into a complementary opening 81 on the processing tube open end 104, forming a liquid tight seal. In one example, a plurality of locking lugs protruding from the filter unit first open end 102 may fit into complementary openings on the sample collection tube 60, coupling the filter unit 70 to the sample collection tube 60 by twist-lock mechanism. Similarly, the filter unit second open end 103 may have a plurality of radiating locking lugs to couple the filter unit 70 to complementary opening on the processing tube 80.

FIG. 6 shows the processing tube 80 with an open end 104 and a closed end 84 opposite first open end 104, similar to processing tube 12 of apparatus 1, shown in FIGS. 1-3. The processing tube open end 104 may reversibly couple to a second removable cap 82, which may prevent the processing fluid or the sample filtrate received by the processing tube from spilling out of the processing tube 80.

In one example of apparatus 2 in use, the sample collected by the integrated collection device 94 integrated to the first removable cap 90 may be received with in a work space 63 in the sample collection tube 60, containing a transport liquid. The first removable cap may stay coupled to the sample collection tube before filtration, during storage and transportation. For filtration and concentration of the sample, the filter unit 70 may twist-lock to the processing tube open end 104 after removable cap 82 is uncoupled. To attach the filter-processing unit to the sample collection tube 60, the first removable cap 90 with the integrated sample collection device 94 may be removed and the filter-processing assembly may be aligned to twist-lock such that the filter unit first open end 102 locking lug 72 is received by the opening 62 on the sample collection tube open end 100, forming a liquid tight seal. The apparatus 2 may now filter the sample through the filter 77 and pass it to the attached processing tube 80 with a processing liquid which may concentrate the sample filtrate. The filtrate may be stored or transported in the processing tube 80 by coupling the second removable cap 84 to the processing tube open end 104.

Referring to FIGS. 10-12, an apparatus 3 for sample collection, filtration, and concentration apparatus is illustrated. Apparatus 3 is substantially similar in form and function to apparatus 2 described in FIGS. 6-9 except for the elimination of a removable cap on a sample collection tube and presence of complementary mating threads instead of a twist-lock mechanism for coupling a filter unit 210 to a sample collection tube 206 and a processing tube 212 with a conical bottom 213. A transport liquid may be present in the sample collection tube 206 and a processing liquid may be present in the sample processing tube 212.

In one embodiment illustrated in FIG. 10, the sample collection tube 206 of apparatus 3 may have a closed end 250 and an open end 251 opposite sample collection tube closed end 250. The sample collection tube first open end 251 may be coupled to a removable cap. The removable cap may have an integrated sample collection device. The apparatus 3 may include the filter unit 210 with a first open end 252 and a filter unit second open end 254 opposite filter unit first open end 252. The filter unit 210 may also include a gas exchange stem 216 at filter unit first open end 252, similar to gas exchange stem 16 of apparatus 1 described in FIGS. 1-6. The filter unit 210 may also include a funnel base stem 215 at the filter unit second open end 254.

For coupling the filter unit 210 to the sample collection tube 206, the filter unit filter open end 252 may have complementary mating threads 218 which may couple the filter unit 210 to the sample collection tube open end 251. Mating threads 219 on the filter unit second open end 254 may couple the filter unit 210 to a processing tube open end 256. The processing tube open end 256 may be coupled to a removable cap 224 when the filter unit 210 is not coupled to the processing tube 212. In one embodiment illustrated in FIGS. 10-12, the sample collection tube open end 251 may have a gripping surface 202 on the outer surface of the sample collection tube 206. The sample processing tube open end 256 may have a gripping surface 203 on the outer wall of the sample processing tube 212. The gripping surface 202 and 203 may be useful for handling the sample collection tube 206 and the sample processing tube 212 during coupling and uncoupling to the filter unit 210. The gripping surfaces 202 and 203 may also be used to grip the assembled apparatus 3.

The filter unit 210 coupled to the sample processing tube 212 and the sample collection tube 206 may be used for sample filtration and concentration. In one example, the apparatus 3 with the filter unit 210 coupled to the sample collection tube 206 and the sample processing tube 212 may be introduced into a centrifuge for filtration.

Figure 13:
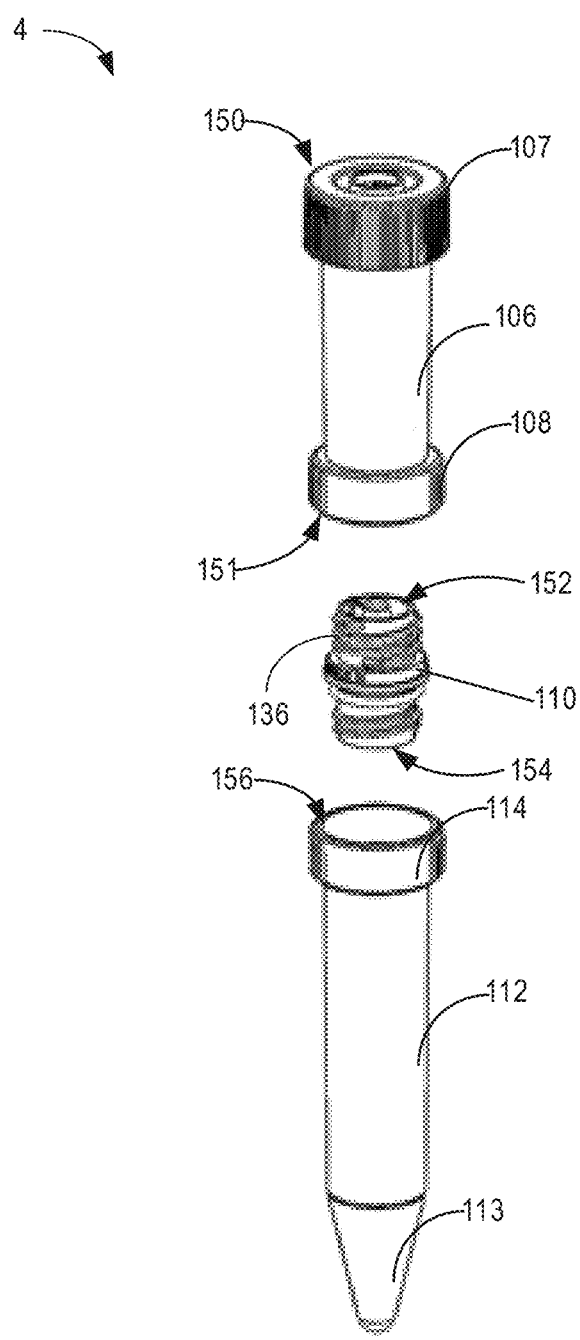
FIG. 13 illustrates another embodiment of a sample collection, filtration and concentration apparatus.
Figure 14:
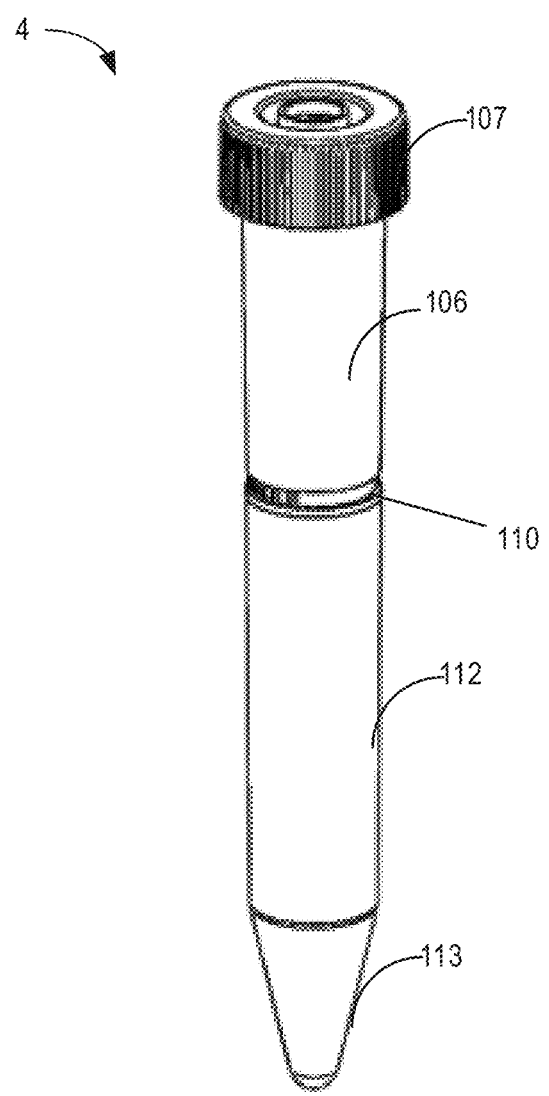
FIG. 14 is a perspective view of the assembled apparatus of FIG. 13.
Figure 15:
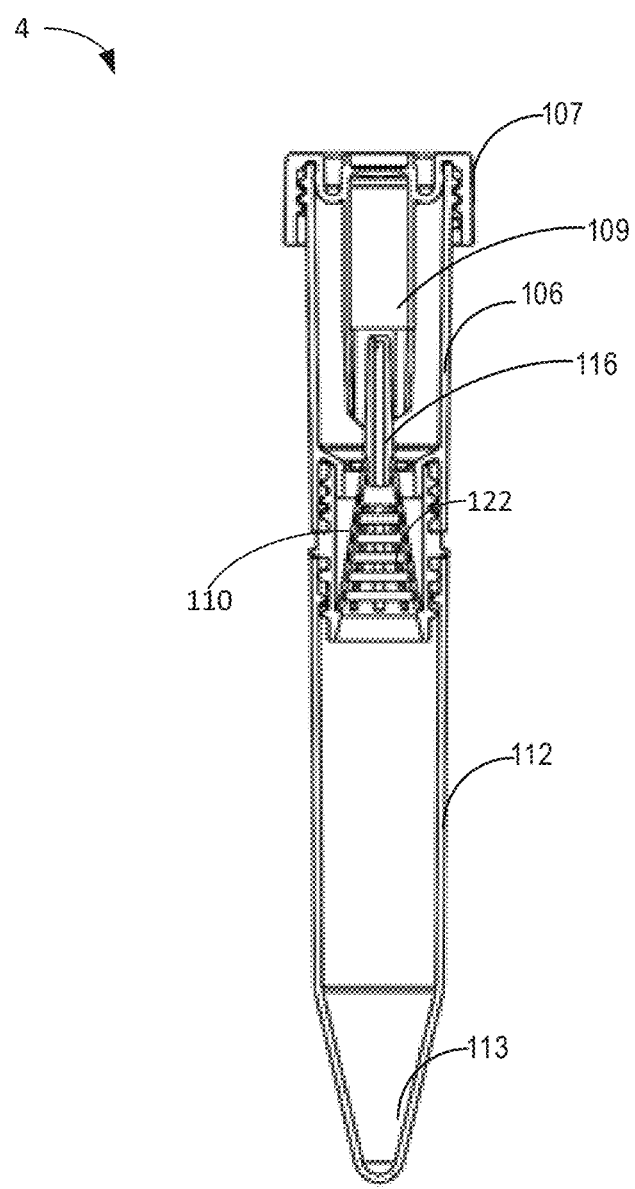
FIG. 15 shows a cross-sectional view of the assembled apparatus of FIG. 14.
Figure 16:
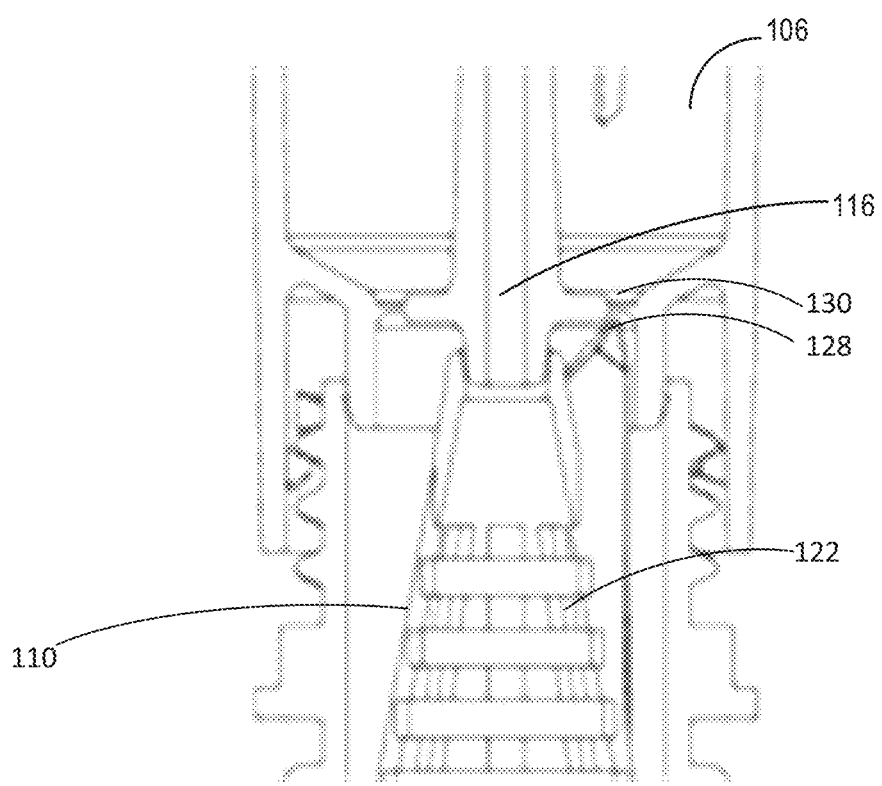
FIG. 16 is a magnified view of the filter unit coupled to the sample processing tube of FIG. 14.

FIGS. 13-16 illustrate an embodiment of a sample collection, filtration, and concentration apparatus 4, substantially similar to the apparatus 1 described in FIGS. 1-5, but with a frangible seal in a sample collection tube open end and a frangible seal puncturing element in a matched filter unit. In one example, apparatus 4 may include a sample collection tube 106 containing a transport liquid, a filter unit 110, and a sample processing tube 112 containing a processing liquid. The sample collection tube 106 may have a first open end 150 and a second open end 151 opposite the sample collection tube first open end 150. The sample collection tube 106 may have a first removable cap 107 with an integrated sample collection device 109, configured to couple the sample collection tube first open end 150, as shown in FIG. 15. A second removable cap 108 may be configured to couple to the sample collection tube second open end 151. The second removable cap 108 may couple to the sample collection tube second open end 151 to protect a frangible seal 130 that may be molded into the sample collection tube second open end 151, as illustrated in FIG. 13. The frangible seal 130 may act as a barrier and prevent the sample and/or the transport liquid from being discharged from the sample collection tube 106.

The filter unit 110 of the apparatus 4 may include a cone shaped filter 122 integral with a threaded union piece 136. The filter unit 110 may have a first open end 152 and a second open end 154 opposite the first open end. The sample collection tube 110 may have an integrated gas exchange stem 116 for equalizing pressure between the sample collection tube 110 and the sample processing tube 112 coupled to the filter unit 110. In one embodiment, the gas exchange stem 116 may be molded as part of the sample collection tube 106 and may engage with the filter unit 110 when the apparatus is assembled. In one example, the gas exchange stem 116 may be a hollow cylindrical tube which may be detachable for the filter unit. In another example, the gas exchange stem 116 may not be detachable from the filter unit 110. In another example, the gas exchange stem 116 may have one or more gas exchange vents. The filter unit 110 may also incorporate a pointed extension 128 in the filter unit first open end 152, as illustrated in FIG. 13. In one example there may be a plurality of pointed extensions 128 on the filter unit first open end 152.

The filter unit 110 may couple to the sample collection tube first open end 150 after removal of first removable cap 107 with an integrated sample collection device 109. In another example, the filter unit may couple to the sample collection tube second open end 151, after removing second removable cap 108. In one embodiment, the coupling of the filter unit 110 to the sample collection tube 106 may be by reversible mating of complementary threads, as illustrated in FIGS. 10 and 12. In one embodiment, as the sample collection tube second open end 151 is coupled onto the filter unit first open end 152, the pointed extension 128 on the filter unit 110 may contact and tear the frangible seal 130 at the sample collection tube second open end 151, releasing the sample from the sample collection tube 106. In one embodiment, the filter unit second open end 154 may be coupled to a processing tube open end 156 to form the filter-processing assembly. The filter-processing assembly may then be coupled to the sample collection tube second open end 151, wherein the projecting element 128 may puncture the frangible seal 130 on the sample collection tube second open end 151, releasing the sample from the sample collection tube, through the filter, and into the processing tube 112. In another example, the filter-processing assembly may be coupled to the sample collection tube first open end 150.

A method 500 for biological sample collection, filtration and concentration using a sample collection, filtration, and concentration apparatus is illustrated in FIG. 17. The method 500 starts at 502 with the collection of a biological sample, such as a fecal sample to be examined for presence of microorganisms. The sample may be collected with a sample collection device integrated to a cap, such as the sample collection device 9 of apparatus 1, the sample collection device 94 of apparatus 2, and the sample collection device 109 of apparatus 4 described in FIGS. 3, 8 and 15, respectively. At 504, the cap with the integrated sample collection device may be coupled to a sample collection tube containing a transport fluid, introducing the sample collection device with the collected sample into the collection tube. The sample received with in the collection tube may come in contact with the transport liquid inside the sample collection tube. The sample may be stored, and transported in the sample collection tube before filtration and concentration.

For subsequent filtration and concentration the method 500 proceeds to 506, where a filter unit may be coupled to a processing tube containing a processing liquid. The coupling may be by reversible mating, as described for apparatus 1, 3 and 4 in FIGS. 1-5, 10-12, and 13-16 or by a twist-lock mechanism, as described for apparatus 2 described in FIG. 6-9. After coupling the filter unit to the processing tube, the method 500 proceeds to 508, where the filtration-processing assembly may be coupled to the sample collection tube containing the sample in the transport liquid. In one example, the removable cap coupled to the sample collection tube may be discarded to expose an open end of the sample collection tube for aligning with the filtration-processing assembly, as indicated at 510. The filter-processing tube unit may be inverted and coupled to the sample collection tube, so that the sample collection tube may be at the lowest point of a vertical arrangement. The coupling mechanism may be by mating of complementary male or female threads, as described for apparatus 1 in FIG. 1. In another embodiment, the coupling may be by twist-locking mechanism as described for apparatus 2 in FIG. 7. The method 500 may proceed to 512, where the filter unit coupled to the collection tube and processing tube may be used for further analysis. In one example, the apparatus may be introduced into a centrifuge for centrifugal filtration and concentration. The processing tube will receive the sample filtrate passed from the sample collection tube through the filter unit into the processing tube. The processing liquid in the processing tube may further concentrate the filtered sample. The processing tube may be uncoupled from the filter unit and coupled to a removable cap, such that the filtrate may be stored and transported in the processing tube for further analysis.

Thus, an apparatus with a filter unit coupled to a sample collection tube with an integrated sample collection device, and coupled to a processing tube containing processing liquid, eliminates the use of separate sample collection jar and additional transfer device. Also, the presence of pre-measured transport liquid in the sample collection tube and processing liquid in the processing tube eliminates the need for additional reagents, minimizing sample handling and diminishing the possibility of contamination of the contact environment.

It is understood that the apparatus described and illustrated herein represents only an example embodiment. It is appreciated by those skilled in the art that various changes and additions may be made to such a sample collection, filtration and concentration apparatus without departing from the spirit and scope of this invention.

In one embodiment, the sample collection, filtration, and processing apparatus may include a sample collection tube containing a transportation liquid with a first open end and a second open end opposite the first open end. The collection tube first open end may be configured to couple to a first removable cap with an integrated sample collection device. The apparatus may also include a sample processing tube containing a processing liquid. The sample processing tube may have an open end and a closed end opposite the processing tube open end. A filter unit may couple to the sample collection tube and the sample processing tube. The filter unit first open end may couple to the collection tube first open end, and the filter unit second open end may couple to the processing tube open end.

In one example, the integrated collection device of the apparatus may be a shank ending in a scoop. In one embodiment, the apparatus may have a removable cap configured to couple with the sample collection tube second open end, wherein the removable cap may have a flared fitting. In another embodiment, the sample collection tube second open end may have a frangible seal. In another example, the filter unit first open end may be configured to couple to the sample collection tube second open end. In a further example, the filter unit may have protruding element to rupture the frangible seal on the sample collection tube second open end upon coupling of the filter unit to the second open end. In another example, the processing tube first open end may be configured to couple to a third removable cap.

In one embodiment, the filter unit of the sample collection, filtration and concentration apparatus may have a cone shaped filter to increase surface available for sample filtration. The filter unit may have a hollow gas exchange stem and a plurality of gas exchange vents on the gas exchange stem. The filter unit may further have a funnel stem for filtrate collection. The funnel stem may prevent liquid from leaking out of the processing tube upon inversion of the processing tube. The filter unit may have an outer frictional gripping surface. In one embodiment, the filter may have a first set of threads at the filter unit first open end for coupling to the sample collection tube, and a second set of threads at the filter unit second open end for coupling to the processing tube. In another embodiment, the filter unit may couple to the collection tube with an integrated sample collection device on one end and to the processing tube on the opposite end by a twist-lock mechanism of coupling.

An example method for sample collection and filtration and concentration may include collecting a sample with a collection device coupled to a first removable cap. The cap with the integrated sample collection device may be coupled to a sample collection tube, introducing the sample into a transport liquid in the collection tube. A filter unit may be coupled to an open end of a processing tube containing a processing liquid to form a filtration-processing unit. The first removable cap may be removed from a collection tube first open end and discarded, followed by coupling the filtration-processing unit to the collection tube first open end such that the filtration-processing assembly aligns with and closes the collection tube first open end. The sample may be filtered through the filter unit and to the processing tube. Filtration may be carried out via centrifugation.

In one embodiment, a sample collection tube containing a transportation liquid and an integrated a sample collection device may be detachable from a matched filter unit coupled to a detachable sample processing tube containing a processing liquid.

In one example, a kit may be provided for assembling a sample collection, filtration and concentration apparatus. The kit may include a sample collection tube with an integrated sample collection device, a sample processing tube and a matched filter unit configured to couple to the sample collection tube on one end and to the processing tube on the second opposite end. The kit may also include a transportation liquid for the sample collection tube and a processing liquid for the sample processing tube.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A sample collection, filtration and processing apparatus, comprising:
   a sample collection tube containing a transportation liquid and having a first open end and a second open end opposite the first open end, the sample collection tube first open end configured to couple to a first removable cap, the first removable cap including an integrated sample collection device;
   a matched sample processing tube containing a processing liquid and having a sample processing tube first open end and a sample processing tube second closed end opposite the sample processing tube first open end; and
   a matched filter unit including a cone shaped filter and having a first open end and a second open end opposite the filter unit first open end, the filter unit first open end configured to couple to the sample collection tube first open end and the filter unit second open end configured to couple to the sample processing tube first open end,
   wherein the cone shaped filter is coupled to a gas exchange stem, the cone shaped filter having a longitudinal axis extending from an apex to a base of the cone shaped filter, and
   wherein a vent that is substantially parallel to the longitudinal axis is formed into a wall of the gas exchange stem, the wall of the gas exchange stem being substantially parallel to a wall of the sample collection tube.

2. The sample collection, filtration and processing apparatus of claim 1, wherein the integrated sample collection device comprises a shank with a scoop.

3. The sample collection, filtration and processing apparatus of claim 1, further comprising a second removable cap configured to couple with and close the sample collection tube second open end.

4. The sample collection, filtration and processing apparatus of claim 3, wherein the second removable cap has a flared fitting.

5. The sample collection, filtration and processing apparatus of claim 1, wherein the filter unit first open end is configured to couple to the sample collection tube second open end.

6. The sample collection, filtration and processing apparatus of claim 1, wherein the sample collection tube second open end has a frangible seal.

7. The sample collection, filtration and processing apparatus of claim 1, wherein the sample processing tube first open end is configured to couple to a third removable cap.

8. The sample collection, filtration and processing apparatus of claim 1, wherein the gas exchange stem is hollow.

9. The sample collection, filtration and processing apparatus of claim 1, where the filter unit includes a protruding element.

10. The sample collection, filtration and processing apparatus of claim 1, where the filter unit includes a funnel stem.

11. The sample collection, filtration and processing apparatus of claim 1, where the filter unit includes a first set of threads at the filter unit first open end for coupling to the sample collection tube, and a second set of threads at the filter unit second open end for coupling to the sample processing tube.

12. A sample collection, filtration and processing apparatus, comprising:
    a sample collection tube containing a transportation liquid and having a first open end and a second closed end opposite the first open end, the sample collection tube first open end configured to couple to a first removable cap, the first removable cap having an integrated sample collection device;
    a matched sample processing tube containing a processing liquid for receiving a sample from the sample collection tube; and
    a matched filter unit disposed between the sample collection tube and the sample processing tube, the matched filter unit including a cone shaped filter,
    wherein the cone shaped filter is coupled to a gas exchange stem, the cone shaped filter having a longitudinal axis extending from an apex to a base of the cone shaped filter, and
    wherein a vent that is substantially parallel to the longitudinal axis is formed into a wall of the gas exchange stem, the wall of the gas exchange stem being substantially parallel to a wall of the sample collection tube.

13. The sample collection, filtration and processing apparatus of claim 12, wherein the matched filter unit is detachable from the sample collection tube.

14. The sample collection, filtration and processing apparatus of claim 12, wherein the matched filter unit is detachable from the sample processing tube.

15. The sample collection, filtration and processing apparatus of claim 12, where the matched filter unit couples to the sample collection tube and the sample processing tube via a twist-lock mechanism.

16. A sample collection, filtration and processing apparatus, comprising:
    a sample collection tube containing a transportation liquid and having a first open end and a second closed end opposite the first open end, the sample collection tube first open end configured to couple to a first removable cap, the first removable cap having an integrated sample collection device;
    a matched sample processing tube containing a processing liquid for receiving a sample from the sample collection tube; and
    a matched filter unit disposed between the sample collection tube and the sample processing tube, the matched filter unit including a cone shaped filter and having a filter unit first open end and a filter unit second open end,
    where the matched filter unit further includes a first set of threads at the filter unit first open end for coupling to the sample collection tube, and a second set of threads at the filter unit second open end for coupling to the sample processing tube
    wherein the cone shaped filter is coupled to a gas exchange stem, the cone shaped filter having a longitudinal axis extending from an apex to a base of the cone shaped filter, and
    wherein a vent that is substantially parallel to the longitudinal axis is formed into a wall of the gas exchange stem, the wall of the gas exchange stem being substantially parallel to a wall of the sample collection tube.

17. The sample collection, filtration and processing apparatus of claim 16, wherein the matched filter unit is detachable from the sample collection tube, and wherein the matched filter unit is detachable from the sample processing tube.

18. The sample collection, filtration and processing apparatus of claim 16, where the gas exchange stem is a funnel stem.

19. The sample collection, filtration and processing apparatus of claim 16, wherein the first removable cap includes an integrated sample collection device comprising a shank with a scoop.

20. The sample collection, filtration and processing apparatus of claim 16, wherein the first open end of the sample processing tube is configured to couple to another removable cap.

* * * * *